United States Patent [19]

Amelio et al.

[11] Patent Number: 4,820,643

[45] Date of Patent: Apr. 11, 1989

[54] PROCESS FOR DETERMINING THE ACTIVITY OF A PALLADIUM-TIN CATALYST

[75] Inventors: William J. Amelio, Austin, Tex.; Kenneth R. Czarnecki, Vestal, N.Y.; Gary K. Lemon, Endwell, N.Y.; Voya Markovich, Endwell, N.Y.; Carlos J. Sambucetti, Croton-on-Hudson, N.Y.; Richard S. Zarr, Apalachin, N.Y.

[73] Assignee: International Business Machines Corporation, Armonk, N.Y.

[21] Appl. No.: 161,233

[22] Filed: Feb. 17, 1988

Related U.S. Application Data

[63] Continuation of Ser. No. 837,917, Mar. 10, 1986, abandoned.

[51] Int. Cl.$^4$ .................. G01N 21/00; G01N 33/20
[52] U.S. Cl. ............................ 436/37; 204/1 T; 204/179; 356/43 L; 436/2; 436/149; 436/164
[58] Field of Search .................. 436/34, 37, 2, 149, 436/164; 204/72, 74, 1 T, 179; 427/97, 304, 305

[56] References Cited

U.S. PATENT DOCUMENTS

| | | | |
|---|---|---|---|
| 1,849,911 | 3/1932 | Curtiss | 436/37 |
| 3,477,018 | 11/1969 | Richardson et al. | 436/37 |
| 3,532,518 | 10/1970 | D'Ottavio | 106/1 |
| 3,562,038 | 2/1971 | Shipley et al. | 427/304 |
| 3,767,583 | 10/1973 | Fadgen, Jr. et al. | 252/79.4 |
| 3,900,320 | 8/1975 | Rolker et al. | 96/35.1 |
| 4,132,605 | 1/1979 | Tench et al. | 204/1 T |
| 4,146,437 | 3/1979 | O'Keefe | 204/1 T |
| 4,318,708 | 3/1982 | Hogberg | 204/179 |
| 4,477,484 | 10/1984 | Paoletti et al. | 427/10 |
| 4,479,852 | 10/1984 | Bindra et al. | 204/1 T |
| 4,608,275 | 8/1986 | Kukanskis | 427/97 |
| 4,639,380 | 1/1987 | Amelio et al. | 427/97 |

OTHER PUBLICATIONS

Levy, "Aspects of the Autocatalytic Plating Reaction", 50th Ann. Tech. Proc., Amer. Electroplaters' Soc., 02-035, 1963, pp. 29–36 and 186–187.
IBM, J. Res. Develop., vol. 28, No. 6, Nov. 1984, Horkans, et al., "Initiation of Electroless Cu Plating on Nonmetallic Surfaces", pp. 690–695.
IBM Technical Disclosure Bulletin, vol. 26, No. 10B, Mar. 1984, Markovich, "Take Time Monitor", p. 5730.
Daniels and Alberty, "Electric Conductance", Physical Chemistry, pp. 374–423.
Van Nostrand's Scientific Encyclopedia, Fourth Edition, "Electrometric Methods of Analysis", 1968, pp. 597–603.
Van Nostrand's Scientific Encyclopedia, Third Edition, 1958, p. 1283.
Pinches, et al., "Cyclic Voltammetric Stripping", Circuits Manufacturing, pp. 36–38 and 40.
Adams, "Electrochemistry at Solid Electrodes", New York, Marvel Dekker, Inc., 1969, pp. 122–143.
Horkans, J., J. Electrochem. Soc. vol. 130 (2) pp. 311–317 Feb. 1983.
Benning A. C., Material Eng. vol (78(1) pp. 46–47 Jan. 1971.

*Primary Examiner*—Michael S. Marcus
*Attorney, Agent, or Firm*—Pollock, Vande Sande & Priddy

[57] ABSTRACT

The effectiveness of a palladium-tin catalyst for subsequent plating thereon is determined by employing cyclic voltammetry.

14 Claims, 1 Drawing Sheet

PROCESS FOR DETERMINING THE ACTIVITY OF A PALLADIUM-TIN CATALYST

This application is a continuation of Ser. No. 837,917, filed on Mar. 10, 1986 abandoned.

DESCRIPTION

1. Technical Field

The present invention is concerned with determining the activity of a palladium-tin colloidal catalyst and is especially concerned with determining the activity of such for subsequent electroless plating of a metal such as copper or nickel thereon.

2. Background Art

In the fabrication of printed circuit cards and boards, a dielectric sheet material is employed as a substrate. A conductive circuit pattern is provided on one or both of the major surfaces of the substrate.

A conductive pattern can be formed on the surface of a substrate using a variety of known techniques. These known techniques include the subtractive technique where a layer of copper is etched to form the desired circuit pattern, the EDB (electroless direct bond) technique where copper is electrolessly plated directly on the surface of the substrate in the desired pattern, and the peel-apart technique where the desired circuit plated up from a thin layer of peel-apart copper.

In any of these techniques, connections between layers are made by means of plated through-holes. In plating such holes, copper must be plated directly on the dielectric substrate (on the walls of the holes). Moreover, if one employs the EDB technique, one must plate directly onto the surface of the substrate.

Since the dielectric substrate is non-conductive, in order to plate on the substrate (either on the walls or the holes, or on the surface of the substrate), the substrate must be seeded or catalyzed prior to the deposition of the metal onto the substrate.

Among the more widely employed procedures for catalyzing a substrate is the use of a stannous chloride sensitizing solution and a palladium chloride activator to form a layer of metallic palladium particles. For instance, one method for catalyzing a dielectric substrate is exemplified by U.S. Pat. No. 3,011,920 which includes sensitizing the substrate by first treating it with a solution of a colloidal metal, accelerating the treatment with a selective solvent to remove protective colloids from the sensitized dielectric substrate, and then electrolessly depositing a metal coating on the sensitized substrate; for example, with copper from a solution of a copper salt and a reducing agent.

The use of palladium-tin colloidal catalysts has been satisfactory for electroless or electroplating thin layers of conductive metals on a non-conductive dielectric substrate for many prior art applications.

However, as the demands for more complex circuitry increases and the requirements of quality of the plated metal likewise increase, the demands upon the quality of the catalyst have also increased. For instance, one recurring problem has been the existence of voids and through-holes and/or poor adhesion or coverage of the dielectric substrate. The quality and ability of the catalyst to coat the substrate has a significant effect on the resulting quality of the plated metal. Accordingly, it is important to be able to distinguish between active and non-active palladium-tin catalysts. Furthermore, it would be desirable to be able to do so in a consistent and reliable manner.

SUMMARY OF THE INVENTION

The process of the present invention provides for distinguishing between active and non-active palladium-tin catalysts. The process of the present invention makes it possible to consistently and reliably characterize the activity of the palladium-tin catalyst.

In particular, the process of the present invention for determining the activity of a palladium-tin colloidal catalyst for the subsequent plating thereon includes determining the cyclic voltammetric Sn—Pd colloid peak of a sample of the catalyst and comparing it to the Sn—Pd colloid peak of a reference Sn—Pd colloidal catalyst known to be active.

BEST AND VARIOUS MODES FOR CARRYING OUT INVENTION

Figure 1:
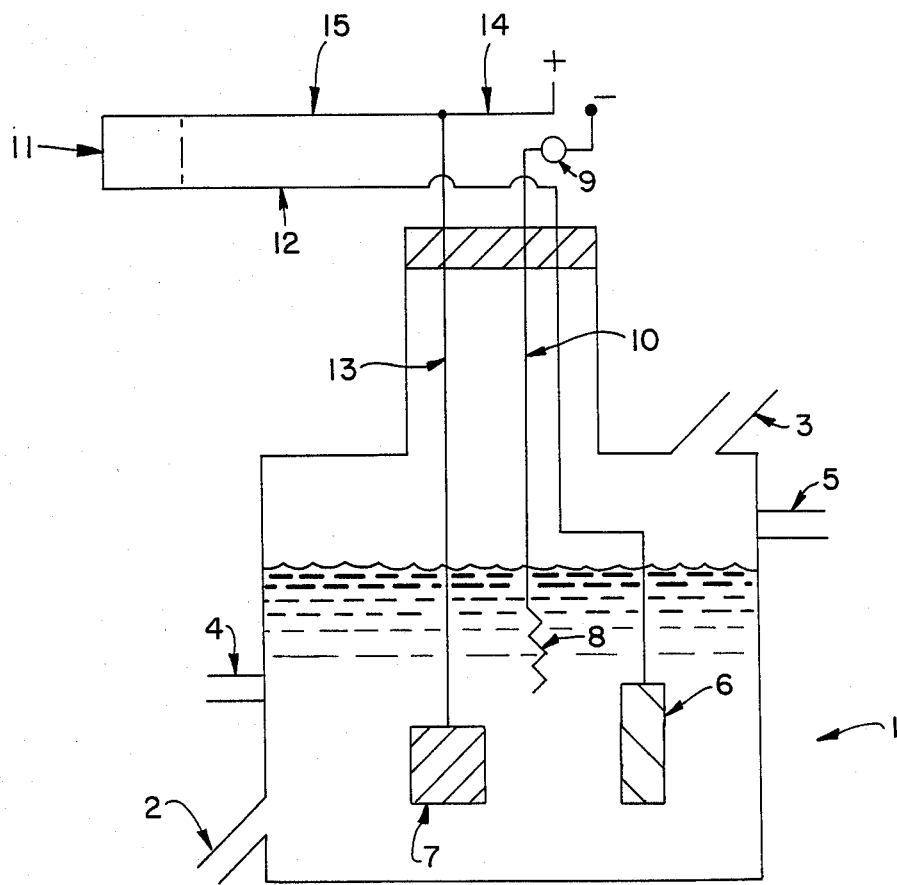
FIG. 1 is a schematic diagram of apparatus suitable for carrying out the voltammertric procedure employed in the process of the present invention.

The present invention is concerned with determining the activity of a palladium-tin catalyst for subsequent plating thereon and especially for electroless plating thereon. Typical palladium-tin colloidal catalysts subjected to the process of the present invention contain about 1.2 to about 2.5 grams/liter of a palladium salt which is preferably $PdCl_2$, about 80 to about 150 grams/liter of a stannous salt which is preferably $SnCl_2.H_2O$, and about 100 to about 150 milliliters per liter of an acid which is preferably HCl. When HCl is provided in the form of a 37% HCl solution in the catalyst, about 290 to about 360 /milliliters of the HCl solution is typically employed. In accordance with the present invention, in order to characterize the palladium-tin catalyst as being active or non-active, a sample of the catalyst is subjected to a plurality of testing procedures.

One of the essential procedures employed in accordance with the present invention involves a cyclic voltammetry method. By employing a cyclic voltammetric procedure, the Sn—Pd colloid peak of the sample is determined. The cyclic voltammetric procedure includes providing a cathode, a reference electrode, and an anode in a suitable container.

The cathode employed is a copper surface covered with the sample to be tested. The preferred copper surface is a one ounce copper foil. A typical size for testing is about 1¾ inch by 1¾ inch square. Prior to coating or covering the copper foil with the sample to be tested, the copper substrate can be immersed in concentrated HCl (about 37% HCl) for about 0.75 to about 1.25 minutes, typical of which is about 1 minute, followed by washing with deionized water in order to prepare the copper substrate for contact with the sample to be tested. Next, the copper foil is immersed in the sample for about 4.75 to about 5.25 minutes, typically about 5 minutes. The foil is then removed from the sample to be tested, washed with deionized water, air-dried under high pressure, and finally, oven-dried for about 14 to about 16 minutes, typically about 15 minutes at about 60° C. to about 70° C. and typically about 65° C.

The seeded copper foil, the cathode, is placed in the test cell along with a reference electrode. Suitable reference electrodes include saturated calomel electrodes and silver/silver chloride. The anode surface is generally platinum or palladium. The anode surface area is usually about equal to the surface area of the cathode to about twice the surface area of the cathode.

The electrolyte employed in the test is a 0.1N perchloric acid aqueous solution ($HClO_4$). About 120 milliliters of such is employed in a container of about 200 cc. The solution is purged with nitrogen for about 4.75 minutes to about 5.25 minutes, typically about 5 minutes in order to remove any oxygen from the solution.

An electric current is passed between the cathode and the anode. The current density is usually in the range of about 0.04 to about 0.21 milliamperes/$cm^2$ of the cathode surface area (one side) and preferably about 0.07 to about 0.21 milliamperes/$cm^2$ of the cathode surface area (one side).

The voltage difference between the cathode and the reference electrode is varied in the direction to thereby remove or oxidize the materials of the cathode and then reversed to recoat or reduce the materials of the cathode.

The voltage is usually varied between about $-0.56$ volts versus a saturated calomel electrode for a platinum anode and increased at a rate of about 10 to about 100 and preferably about 20 to about 30 and most typically about 26 millivolts per second, up to about $+0.04$ volts and is then reversed back to a voltage of about $-0.56$ volts. Generally about $1\frac{1}{2}$ complete cycles are employed per test. During this time, the electrodes are maintained in a stationary position. The voltage versus the current are recorded and plotted. The Pd—Sn colloid peak for this set-up is at about $-0.28$ volts. The peak of the Pd—Sn colloid is compared to the Sn—Pd colloid peak of a reference seeder known to be active. If the peak is not at least equal to that of the reference catalyst or seeder, then the catalyst is rejected.

Reference to FIG. 1 illustrates apparatus suitable for carrying out the cyclic voltammertic procedure employed in the process of the present invention. In particular, there is shown a container designated by 1 containing the electrodes and electrolyte. The electrolyte is conveyed to the testing apparatus via conduit 3 and exits the testing apparatus via conduit 2. Nitrogen is injected into the bath via conduit 4 and exits via conduit 5. Immersed in the electrolyte is the reference electrode 6, the seeded cathode 7, and the metal anode (counterelectrode) 8. The anode 8 is electrically connected to ammeter 9 and to the negative pole of a controlled current-potential source (not shown) via ohmic connection 10. Reference electrode 6 is electrically connected to a potential recording device 11 via ohmic connection 12. The cathode 7 is electrically connected to the positive pole of a controlled current-potential source (not shown) via ohmic connectors 13 and 15. The cathode 7 is electrically connected to the potential recording device 11 via connectors 13 and 14. Potential recording device 11 records the voltage difference between the reference electrode 6 and the cathode or working electrode 7.

Moreover, in accordance with preferred aspects of the present invention, to further assure activity of the palladium-tin catalyst, additional tests are carried out.

In particular, another test performed to characterize the catalyst composition in accordance with the present invention is to measure the optical density of a coating of the seeder on glass substrate and comparing it to that measured for reference seeder composition. The procedure includes employing glass slides such as those of about 1 inch by 3 inches, cleaning for about 0.75 to about 1.25 minutes, typically 1 minute in hot K-2 cleaner, followed by a hot deionized water rinse for about 1.75 to about 2.25 minutes, typically about 2 minutes.

Next, the slide is coated immersed in a bath containing Reten, typically about 0.05 weight percent in 2% $H_2SO_4$ aqueous solution for about 0.75 to about 1.25 minutes, typically 1 minute. The coated slide is then rinsed in deionized water for about 0.75 to about 1.25 minutes, typically about 1 minute and coated with the seeder by immersion in the seeder composition for about 2.75 to about 3.25 minutes, typically about 3 minutes. The slide is then washed for about 1.75 to about 2.25 minutes, typically about 2 minutes in deionized water and dried for about 14 to about 16 minutes, typically about 15 minutes in an oven at about 60° C. to about 70° C.; typically about 65° C. The optical density can be measured using a densitometer such as a McBeth Densitometer. The light transmission values should be about 40% to about 72% with about 58% being preferred.

The activity of the catalyst composition is further verified by determining the amount of time for plating onto the glass slides treated as above. Such glass slides containing the seeder composition are prepared for the plating by first cleaning, such as by contacting the slides in hydrochloric acid (e.g. 8% concentation) for about 4 to about 6 seconds, typically about 5 seconds to activate the catalyst, then in deionized water for about 4 to about 6 seconds, typically about 5 seconds. The slides are then placed in an electroless copper plating bath at a temperature of about 70°–80° C., typically about 72° C.$\pm 2$° C. for about 3 to about 5 minutes, typically about 4 minutes. The quality of the coating is then compared to that obtained in the same bath by using a reference seeded composition. The glass plating can also be determined by placing both the glass slides containing the seeder compositions of the sample to be tested, as well as a reference seeder composition in an electroless plating bath and removing the slides upon one of the slides being coated with the copper. Then the quality and thickness of the coatings are compared.

Moreover, the activity of the seeder is verified by comparing the take time for the electroless plating to occur, as compared to the take time of a reference seeder. This can be determined by placing cards containing conductive lines referred to as resistance or Rho cards with sample and reference seeders compositions coated thereon in the same manner as the glass slides hereinabove were coated. The cards are attached to an ohmmeter which, in turn, is connected to a chart recorder. The cards are placed into an electroless plating bath which is at a bath temperature of about 70° to about 80° C., typically about 72° C.$\pm 2$° C. The take time is recorded on the chart and is calculated from the break point in the recorder tracing which indicates an electrical connection between the conductive lines on the card. This take time test provides for an understanding of the activity of the bath by providing a time versus copper deposition relationship.

Having thus described our invention, what we claim as new and desire to secure by Letters Patent is:

1. A method for characterizing as active or nonactive a palladium-tin colloidal catalyst for subsequent plating thereon which comprises:

determining the cyclic voltammetric Sn—Pd colloid peak of a dried sample of said catalyst;

comparing the cyclic voltammetric Sn—Pd colloid peak to the cyclic voltammertric Sn—Pd colloid peak of an active reference palladium-tin colloid catalyst known to be active, determining the optical density of a coating of a sample of said catalyst on a glass substrate and comparing it to reference optical density of a reference palladium-tin colloid catalyst, determining the time for electrolessly plating a metal onto a glass substrate catalysed with a sample of the catalyst and comparing the time to reference time of a reference palladium-tin colloid catalyst; and determining the thickness of the coating on glass and comparing it to a reference coating of a reference palladium-tin colloid catalyst; and a catalyst is determined to be active when the following conditions are obtained; said Sn—Pd colloid peak must be at least equal to that of the said reference to be considered active; the time for electrolessly plating be at least as fast as that of the said reference to be considered active; and the thickness being at least as thick as that for the said reference to be considered active; and said optical density is such as to provide light transmission of about 40% to about 72% to be considered active.

2. The method of claim 1 wherein cyclic voltammetric Sn—Pd colloid peak is determined by varying the voltage between about −0.56 volts versus a saturated calomel electrode to about +0.04 volts and then back to about −0.56 volts.

3. The method of claim 2 wherein said Pd—Sn colloid peak is at about −0.28 volts.

4. The method of claim 3 wherein an electrolyte is used in determining said cyclic voltammetric Sn—Pd colloid peak and said electrolyte is about a 0.1N perchloric acid aqueous solution.

5. The method of claim 1 wherein an electrolyte is used in determining said cyclic voltammetric Sn—Pd colloid peak and said electrolyte is about a 0.1N perchloric acid aqueous solution.

6. The method of claim 1 wherein said Sn—Pd colloid peak is determined by employing electrodes that are maintained in a stationary position during the determination of said colloid peak.

7. The method of claim 1 wherein said metal is copper.

8. The method of claim 1 which further includes determining the take time for electroless plating of a metal onto a resistance card and comparing it to a reference take time.

9. The method of claim 8 wherein said metal is copper.

10. The method of claim 1 wherein said palladium-tin catalyst contains about 1.2 to about 2.5 grams/liter of a palladium salt and about 80 to about 150 grams/liter of a stannous salt.

11. The method of claim 10 wherein said palladium salt is $PdCl_2$ and said stannous salt is $SnCl_2.2H_2O$.

12. The method of claim 1 wherein said cyclic voltammetric Sn—Pd colloid peak is determined by varying the voltage for about 1½ complete cycles.

13. The method of claim 1 wherein said cycle voltammetric Sn—Pd colloid peak is determined by employing as cathode a copper foil coated with the catalyst being tested, a reference electrode, and a cathode.

14. The method of claim 13 wherein said copper foil is one ounce copper foil.

* * * * *